United States Patent
Johnson et al.

(10) Patent No.: US 10,136,954 B2
(45) Date of Patent: Nov. 27, 2018

(54) SURGICAL TOOL SYSTEMS AND METHOD

(71) Applicant: GLOBUS MEDICAL, INC., Audubon, PA (US)

(72) Inventors: Norbert Johnson, North Andover, MA (US); Robert Stevens, North Chelmsford, MA (US); Hisham Salem, Newton, MA (US); Yuan Cheng, Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 233 days.

(21) Appl. No.: 15/180,135

(22) Filed: Jun. 13, 2016

(65) Prior Publication Data
US 2017/0354468 A1 Dec. 14, 2017

Related U.S. Application Data

(63) Continuation-in-part of application No. 15/095,883, filed on Apr. 11, 2016, which is a continuation-in-part
(Continued)

(51) Int. Cl.
*A61B 34/30* (2016.01)
*A61B 34/20* (2016.01)
(Continued)

(52) U.S. Cl.
CPC .............. *A61B 34/30* (2016.02); *A61B 5/061* (2013.01); *A61B 5/062* (2013.01); *A61B 34/10* (2016.02);
(Continued)

(58) Field of Classification Search
None
See application file for complete search history.

(56) References Cited

U.S. PATENT DOCUMENTS

| 4,511,825 A | 4/1985 | Klino |
| 4,697,661 A | 10/1987 | Pajerski et al. |

(Continued)

FOREIGN PATENT DOCUMENTS

| EP | 0744633 A2 | 11/1996 |
| EP | 2286729 A2 | 2/2011 |

(Continued)

OTHER PUBLICATIONS

US 8,231,638, 07/2012, Swarup et al. (withdrawn)
(Continued)

*Primary Examiner* — Truc M Do

(57) ABSTRACT

Devices, Systems, and Methods for controlled movement of the robot system. The surgical robot system may include a robot having a robot base, a robot arm coupled to the robot base, and an end-effector coupled to the robot arm. The robot may include a plurality of omni-directional wheels affixed to the robot base allowing multiple-axis movement of the robot. The robot may further include sensors for detecting a desired movement of the robot base and a control system responsive to the plurality of sensors for controlling the multiple-axis movement of the robot by actuating two or more of the plurality of omni-directional wheels.

20 Claims, 16 Drawing Sheets

Related U.S. Application Data of application No. 14/062,707, filed on Oct. 24, 2013, which is a continuation-in-part of application No. 13/924,505, filed on Jun. 21, 2013, now Pat. No. 9,782,229.

(60) Provisional application No. 61/662,702, filed on Jun. 21, 2012, provisional application No. 61/800,527, filed on Mar. 15, 2013.

(51) Int. Cl.
*A61B 90/98* (2016.01)
*A61B 5/06* (2006.01)
*B25J 5/00* (2006.01)
*B60B 19/00* (2006.01)
*A61B 34/00* (2016.01)
*A61B 34/10* (2016.01)
*B25J 13/06* (2006.01)
*A61B 17/00* (2006.01)
*A61B 90/00* (2016.01)

(52) U.S. Cl.
CPC .............. *A61B 34/20* (2016.02); *A61B 34/74* (2016.02); *A61B 90/98* (2016.02); *B25J 5/007* (2013.01); *B25J 13/065* (2013.01); *B60B 19/003* (2013.01); *A61B 2017/00212* (2013.01); *A61B 2034/2046* (2016.02); *A61B 2034/2051* (2016.02); *A61B 2034/2055* (2016.02); *A61B 2034/742* (2016.02); *A61B 2090/064* (2016.02); *A61B 2090/3979* (2016.02); *A61B 2090/3983* (2016.02)

(56) References Cited

U.S. PATENT DOCUMENTS

| | | | |
|---|---|---|---|
| 5,354,314 A | 10/1994 | Hardy et al. | |
| 5,397,323 A | 3/1995 | Taylor et al. | |
| 5,425,069 A | 6/1995 | Pellegrino et al. | |
| 5,772,594 A | 6/1998 | Barrick | |
| 5,791,908 A | 8/1998 | Gillio | |
| 5,820,559 A | 10/1998 | Ng et al. | |
| 5,825,982 A | 10/1998 | Wright et al. | |
| 5,887,121 A | 3/1999 | Funda et al. | |
| 5,911,449 A | 6/1999 | Daniele et al. | |
| 5,951,475 A | 9/1999 | Gueziec et al. | |
| 6,012,216 A | 1/2000 | Esteves et al. | |
| 6,033,415 A | 3/2000 | Mittelstadt et al. | |
| 6,080,181 A | 6/2000 | Jensen et al. | |
| 6,106,511 A | 8/2000 | Jensen | |
| 6,122,541 A | 9/2000 | Cosman et al. | |
| 6,157,853 A | 12/2000 | Blume et al. | |
| 6,167,145 A | 12/2000 | Foley et al. | |
| 6,167,292 A | 12/2000 | Badano et al. | |
| 6,201,984 B1 | 3/2001 | Funda et al. | |
| 6,205,411 B1 | 3/2001 | DiGioia, III et al. | |
| 6,212,419 B1 | 4/2001 | Blume et al. | |
| 6,231,565 B1 | 5/2001 | Tovey et al. | |
| 6,236,875 B1 | 5/2001 | Bucholz et al. | |
| 6,246,900 B1 | 6/2001 | Cosman et al. | |
| 6,276,471 B1 | 8/2001 | Kratzenberg et al. | |
| 6,301,495 B1 | 10/2001 | Gueziec et al. | |
| 6,312,435 B1 | 11/2001 | Wallace et al. | |
| 6,314,311 B1 | 11/2001 | Williams et al. | |
| 6,322,567 B1 | 11/2001 | Mittelstadt et al. | |
| 6,325,808 B1 | 12/2001 | Bernard et al. | |
| 6,340,363 B1 | 1/2002 | Bolger et al. | |
| 6,377,011 B1 | 4/2002 | Ben-Ur | |
| 6,379,302 B1 | 4/2002 | Kessman et al. | |
| 6,402,762 B2 | 6/2002 | Hunter et al. | |
| 6,424,885 B1 | 7/2002 | Niemeyer et al. | |
| 6,447,503 B1 | 9/2002 | Wynne et al. | |
| 6,451,027 B1 | 9/2002 | Cooper et al. | |
| 6,477,400 B1 | 11/2002 | Barrick | |
| 6,484,049 B1 | 11/2002 | Seeley et al. | |
| 6,490,467 B1 | 12/2002 | Bucholz et al. | |
| 6,490,475 B1 | 12/2002 | Seeley et al. | |
| 6,491,127 B1 * | 12/2002 | Holmberg | B60K 7/0007 180/21 |
| 6,499,488 B1 | 12/2002 | Hunter et al. | |
| 6,507,751 B2 | 1/2003 | Blume et al. | |
| 6,535,756 B1 | 3/2003 | Simon et al. | |
| 6,560,354 B1 | 5/2003 | Maurer, Jr. et al. | |
| 6,565,554 B1 | 5/2003 | Niemeyer | |
| 6,587,750 B2 | 7/2003 | Gerbi et al. | |
| 6,614,453 B1 | 9/2003 | Suri et al. | |
| 6,636,757 B1 | 10/2003 | Jascob et al. | |
| 6,645,196 B1 | 11/2003 | Nixon et al. | |
| 6,669,635 B2 | 12/2003 | Kessman et al. | |
| 6,701,173 B2 | 3/2004 | Poston et al. | |
| 6,782,287 B2 | 8/2004 | Grzeszczuk et al. | |
| 6,783,524 B2 | 8/2004 | Anderson et al. | |
| 6,786,896 B1 | 9/2004 | Madhani et al. | |
| 6,788,018 B1 | 9/2004 | Blumenkranz | |
| 6,804,581 B2 | 10/2004 | Wang et al. | |
| 6,823,207 B1 | 11/2004 | Jensen et al. | |
| 6,827,351 B2 | 12/2004 | Graziani et al. | |
| 6,837,892 B2 | 1/2005 | Shoham | |
| 6,839,612 B2 | 1/2005 | Sanchez et al. | |
| 6,856,826 B2 | 2/2005 | Seeley et al. | |
| 6,856,827 B2 | 2/2005 | Seeley et al. | |
| 6,871,715 B1 | 3/2005 | Diaz Carmena et al. | |
| 6,879,880 B2 | 4/2005 | Nowlin et al. | |
| 6,892,090 B2 | 5/2005 | Verard et al. | |
| 6,920,347 B2 | 7/2005 | Simon et al. | |
| 6,968,224 B2 | 11/2005 | Kessman et al. | |
| 6,978,166 B2 | 12/2005 | Foley et al. | |
| 6,991,627 B2 | 1/2006 | Madhani et al. | |
| 6,999,852 B2 | 2/2006 | Green | |
| 7,007,699 B2 | 3/2006 | Martinelli et al. | |
| 7,063,705 B2 | 6/2006 | Young et al. | |
| 7,072,707 B2 | 7/2006 | Galloway, Jr. et al. | |
| 7,083,615 B2 | 8/2006 | Peterson et al. | |
| 7,097,640 B2 | 8/2006 | Wang et al. | |
| 7,130,676 B2 | 10/2006 | Barrick | |
| 7,139,418 B2 | 11/2006 | Abovitz et al. | |
| 7,139,601 B2 | 11/2006 | Bucholz et al. | |
| 7,155,316 B2 | 12/2006 | Sutherland et al. | |
| 7,164,968 B2 | 1/2007 | Treat et al. | |
| 7,167,738 B2 | 1/2007 | Schweikard et al. | |
| 7,169,141 B2 | 1/2007 | Brock et al. | |
| 7,172,627 B2 | 2/2007 | Fiere et al. | |
| 7,239,940 B2 | 7/2007 | Wang et al. | |
| 7,248,914 B2 | 7/2007 | Hastings et al. | |
| 7,302,288 B1 | 11/2007 | Schellenberg | |
| 7,313,430 B2 | 12/2007 | Urquhart et al. | |
| 7,318,827 B2 | 1/2008 | Leitner et al. | |
| 7,319,897 B2 | 1/2008 | Leitner et al. | |
| 7,327,865 B2 | 2/2008 | Fu et al. | |
| 7,331,967 B2 | 2/2008 | Lee et al. | |
| 7,333,642 B2 | 2/2008 | Green | |
| 7,339,341 B2 | 3/2008 | Oleynikov et al. | |
| 7,348,747 B1 * | 3/2008 | Theobold | B25J 5/005 318/568.11 |
| 7,366,562 B2 | 4/2008 | Dukesherer et al. | |
| 7,379,790 B2 | 5/2008 | Toth et al. | |
| 7,386,365 B2 | 6/2008 | Nixon | |
| 7,422,592 B2 | 9/2008 | Morley et al. | |
| 7,435,216 B2 | 10/2008 | Kwon et al. | |
| 7,440,793 B2 | 10/2008 | Chauhan et al. | |
| 7,466,303 B2 | 12/2008 | Yi et al. | |
| 7,493,153 B2 | 2/2009 | Ahmed et al. | |
| 7,505,617 B2 | 3/2009 | Fu et al. | |
| 7,533,892 B2 | 5/2009 | Schena et al. | |
| 7,542,791 B2 | 6/2009 | Mire et al. | |
| 7,555,331 B2 | 6/2009 | Viswanathan | |
| 7,567,834 B2 | 7/2009 | Clayton et al. | |
| 7,594,912 B2 | 9/2009 | Cooper et al. | |
| 7,606,613 B2 | 10/2009 | Simon et al. | |
| 7,607,440 B2 | 10/2009 | Coste-Maniere et al. | |
| 7,630,752 B2 | 12/2009 | Viswanathan | |
| 7,630,753 B2 | 12/2009 | Simon et al. | |

(56) References Cited

U.S. PATENT DOCUMENTS

| | | |
|---|---|---|
| 7,643,862 B2 | 1/2010 | Schoenefeld |
| 7,660,623 B2 | 2/2010 | Hunter et al. |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,711,406 B2 | 5/2010 | Kuhn et al. |
| 7,720,523 B2 | 5/2010 | Omernick et al. |
| 7,742,801 B2 | 6/2010 | Neubauer et al. |
| 7,751,865 B2 | 7/2010 | Jascob et al. |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,035,685 B2 | 10/2011 | Jensen |
| 8,046,054 B2 | 10/2011 | Kim et al. |
| 8,046,057 B2 | 10/2011 | Clarke |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,092,370 B2 | 1/2012 | Roberts et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,120,301 B2 * | 2/2012 | Goldberg .............. A61B 34/30 318/432 |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,263,933 B2 | 9/2012 | Zeile |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 * | 4/2013 | Mohr .................... A61B 34/37 606/130 |
| 8,442,738 B2 | 5/2013 | Patmore |
| 8,450,694 B2 | 5/2013 | Baviera et al. |
| 8,452,447 B2 | 5/2013 | Nixon |
| RE44,305 E | 6/2013 | Foley et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |

(56) References Cited

U.S. PATENT DOCUMENTS

| | | |
|---|---|---|
| 8,551,116 B2 | 10/2013 | Julian et al. |
| 8,556,807 B2 | 10/2013 | Scott et al. |
| 8,556,979 B2 | 10/2013 | Glerum et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,676,420 B2 | 3/2014 | Kume et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,700,123 B2 | 4/2014 | Okamura et al. |
| 8,706,086 B2 | 4/2014 | Norrman et al. |
| 8,706,185 B2 | 4/2014 | Foley et al. |
| 8,706,301 B2 | 4/2014 | Zhao et al. |
| 8,717,430 B2 | 5/2014 | Simon et al. |
| 8,734,432 B2 | 5/2014 | Tuma et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,792,704 B2 | 7/2014 | Isaacs |
| 8,800,838 B2 | 8/2014 | Shelton, IV |
| 8,808,164 B2 | 8/2014 | Hoffman et al. |
| 8,812,077 B2 | 8/2014 | Dempsey |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 9,554,953 B2 | 1/2017 | Dirauf et al. |
| 9,668,768 B2* | 6/2017 | Piron ................. A61B 17/3421 |
| 9,827,054 B2* | 11/2017 | Richmond ............. A61B 34/20 |
| 9,862,090 B2* | 1/2018 | Kennedy .................... B25J 9/06 |
| 9,907,721 B2* | 3/2018 | Morbi ..................... A61H 3/00 |
| 2001/0036302 A1 | 11/2001 | Miller |
| 2001/0047895 A1* | 12/2001 | De Fazio ............. B62D 57/024 |
| | | 180/22 |
| 2002/0035321 A1 | 3/2002 | Bucholz et al. |
| 2003/0055049 A1 | 3/2003 | Brock |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0143089 A1* | 6/2010 | Hvass .................... G05D 1/027 |
| | | 414/754 |
| 2010/0152899 A1* | 6/2010 | Chang ..................... B25J 9/162 |
| | | 700/262 |

(56) References Cited

U.S. PATENT DOCUMENTS

| | | |
|---|---|---|
| 2010/0228117 A1 | 9/2010 | Hartmann |
| 2010/0228265 A1 | 9/2010 | Prisco |
| 2010/0249571 A1 | 9/2010 | Jensen et al. |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0046668 A1 | 2/2012 | Gantes |
| 2012/0053597 A1 | 3/2012 | Anvari et al. |
| 2012/0059248 A1 * | 3/2012 | Holsing .............. A61B 1/2676 600/424 |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345718 A1 | 12/2013 | Crawford et al. |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0052153 A1 * | 2/2014 | Griffiths .............. A61B 34/70 606/130 |
| 2014/0058406 A1 | 2/2014 | Tsekos |
| 2014/0066944 A1 | 3/2014 | Taylor et al. |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0188273 A1 * | 7/2014 | Khoukhi .............. B25J 9/162 700/250 |
| 2014/0194699 A1 | 7/2014 | Roh et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275955 A1 | 9/2014 | Crawford et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371973 A1 * | 12/2014 | Pfaff .............. G05D 1/0088 701/23 |
| 2014/0379130 A1 | 12/2014 | Lee et al. |

(56) References Cited

U.S. PATENT DOCUMENTS

| | | | | |
|---|---|---|---|---|
| 2015/0051519 A1* | 2/2015 | Morbi | ............... | A61H 3/00 |
| | | | | 601/26 |
| 2015/0100066 A1* | 4/2015 | Kostrzewski | .......... | A61B 34/30 |
| | | | | 606/130 |
| 2017/0269607 A1* | 9/2017 | Fulop | ............ | G05D 1/0287 |

FOREIGN PATENT DOCUMENTS

| | | | |
|---|---|---|---|
| JP | 898843 A | 4/1996 | |
| JP | 8313304 A | 11/1996 | |
| WO | 02071369 A1 | 9/2002 | |
| WO | 2012018816 A3 | 2/2012 | |

OTHER PUBLICATIONS

Edward Ramsden, Hall Effect Sensors; Theory and Application (2nd Edition), pp. 107-130, http://store.elsevier.com/Hall-Effect-Sensors/Edward-Ramsden/isbn-9780080523743/. Feb. 28, 2006.

Shuanghui, Hao et al., Study on a novel absolute magnetic encoder, Robotice and Biomemetics, 2009, Robio, 2009. IEEE, International Conference on IEEE. pp. 1773-1776, Feb. 22, 2009.

Eric M. Yeatmann et al., "Use of Scanned Detection in Optical Position Encoders", IEEE, Transactions of Instrumentation and Measurement. vol. 53, No. 1, pp. 37-44. http://www3.imperial.ac.uk/pls/portallive/docs/1/375913.PDF. Feb. 28, 2004.

\* cited by examiner

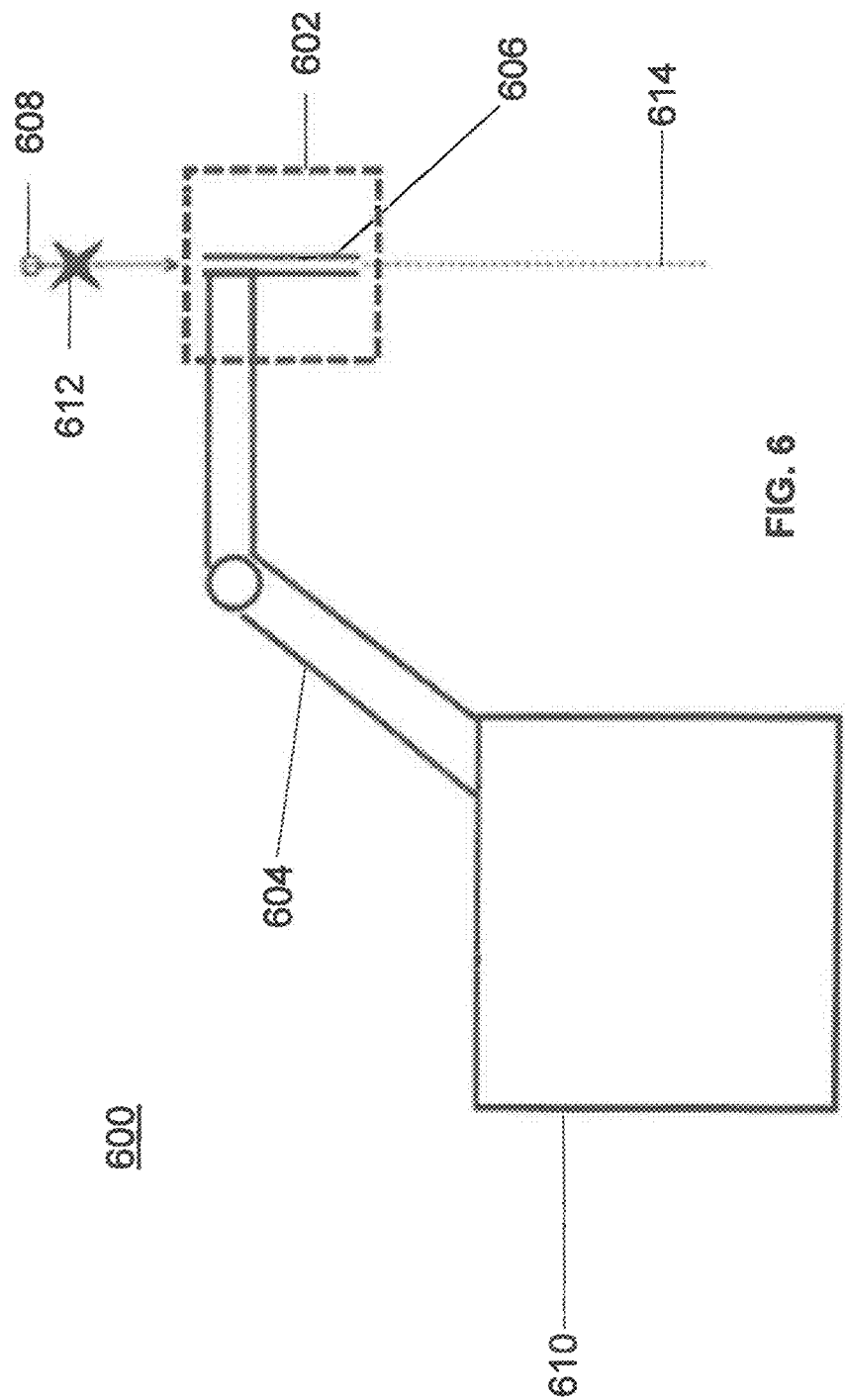

SURGICAL TOOL SYSTEMS AND METHOD

CROSS REFERENCE TO RELATED APPLICATIONS

This application is a continuation-in-part of U.S. patent application Ser. No. 15/095,883, filed Apr. 11, 2016, which is a continuation-in-part of U.S. patent application Ser. No. 14/062,707, filed on Oct. 24, 2013, which is a continuation-in-part application of U.S. patent application Ser. No. 13/924,505, filed on Jun. 21, 2013, which claims priority to provisional application No. 61/662,702 filed on Jun. 21, 2012 and claims priority to provisional application No. 61/800,527 filed on Mar. 15, 2013, all of which are incorporated by reference herein in their entireties for all purposes.

FIELD

The present disclosure relates to medical robotic systems, and more particularly, controlled movement of the robot system or components thereof.

BACKGROUND

Position recognition systems are used to determine the position of and track a particular object in 3-dimensions (3D). In robot assisted surgeries, for example, certain objects, such as surgical instruments, need to be tracked with a high degree of precision as the instrument is being positioned and moved by a robot or by a physician, for example.

Infrared signal based position recognition systems may use passive and/or active sensors or markers for tracking the objects. In passive sensors or markers, objects to be tracked may include passive sensors, such as reflective spherical balls, which are positioned at strategic locations on the object to be tracked. Infrared transmitters transmit a signal, and the reflective spherical balls reflect the signal to aid in determining the position of the object in 3D. In active sensors or markers, the objects to be tracked include active infrared transmitters, such as light emitting diodes (LEDs), and thus generate their own infrared signals for 3D detection.

With either active or passive tracking sensors, the system then geometrically resolves the 3-dimensional position of the active and/or passive sensors based on information from or with respect to one or more of the infrared cameras, digital signals, known locations of the active or passive sensors, distance, the time it took to receive the responsive signals, other known variables, or a combination thereof.

One problem is ensuring that the location of the robot is accurate and controlling movement of the robot system or other medical equipment, for example, around the operating room environment.

SUMMARY

To meet this and other needs, devices, systems, and methods for controlling movement of the robot-assisted surgeries, for example, with omni-directional wheels is provided.

According to one embodiment, a surgical robot system includes a robot having a robot base, a robot arm coupled to the robot base, and an end-effector coupled to the robot arm, the end-effector including a plurality of tracking markers detectable by at least one camera; a plurality of omni-directional wheels affixed to the robot base allowing multiple-axis movement of the robot; a plurality of sensors for detecting a desired movement of the robot base; and a control system responsive to the plurality of sensors for controlling the multiple-axis movement of the robot by actuating two or more of the plurality of omni-directional wheels.

According to another embodiment, a surgical robot system includes a robot having a robot base, a robot arm coupled to the robot base, and an end-effector coupled to the robot arm, the end-effector including a guide tube for receiving at least one instrument; a plurality of omni-directional wheels attached to the robot base allowing three-axis movement of the robot in a general area of a plane; a plurality of sensors for detecting a desired movement of the robot base; and a control system responsive to the plurality of sensors for controlling the three-axis movement of the robot base by actuating two or more of the plurality of omni-directional wheels.

According to yet another embodiment, a surgical robot system includes A surgical robot system comprising: a robot having a robot base, a robot arm coupled to the robot base, and an end-effector coupled to the robot arm, the end-effector including a plurality of tracking markers detectable by at least one camera; and a plurality of omni-directional wheels affixed to the robot base allowing multiple-axis movement of the robot, wherein each of the plurality of omni-directional wheels includes a central hub with a plurality of rollers mounted to the central hub.

DESCRIPTION OF THE DRAWINGS

FIG. 6 illustrates a surgical robot in accordance with an exemplary embodiment;

DETAILED DESCRIPTION

Figure 1:
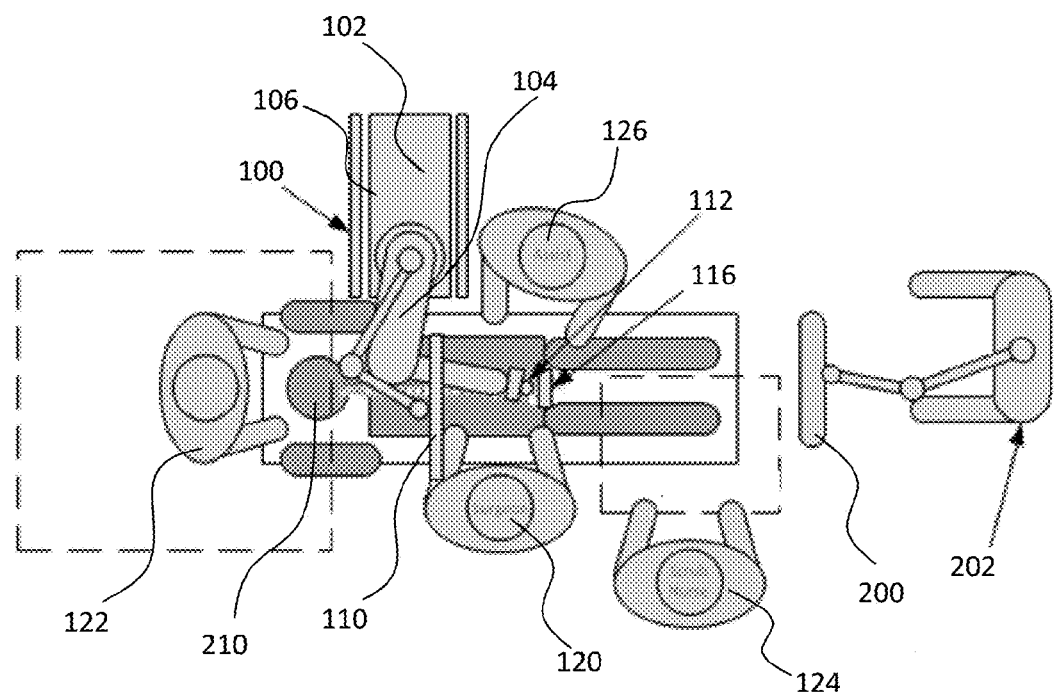
FIG. 1 is an overhead view of a potential arrangement for locations of the robotic system, patient, surgeon, and other medical personnel during a surgical procedure.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
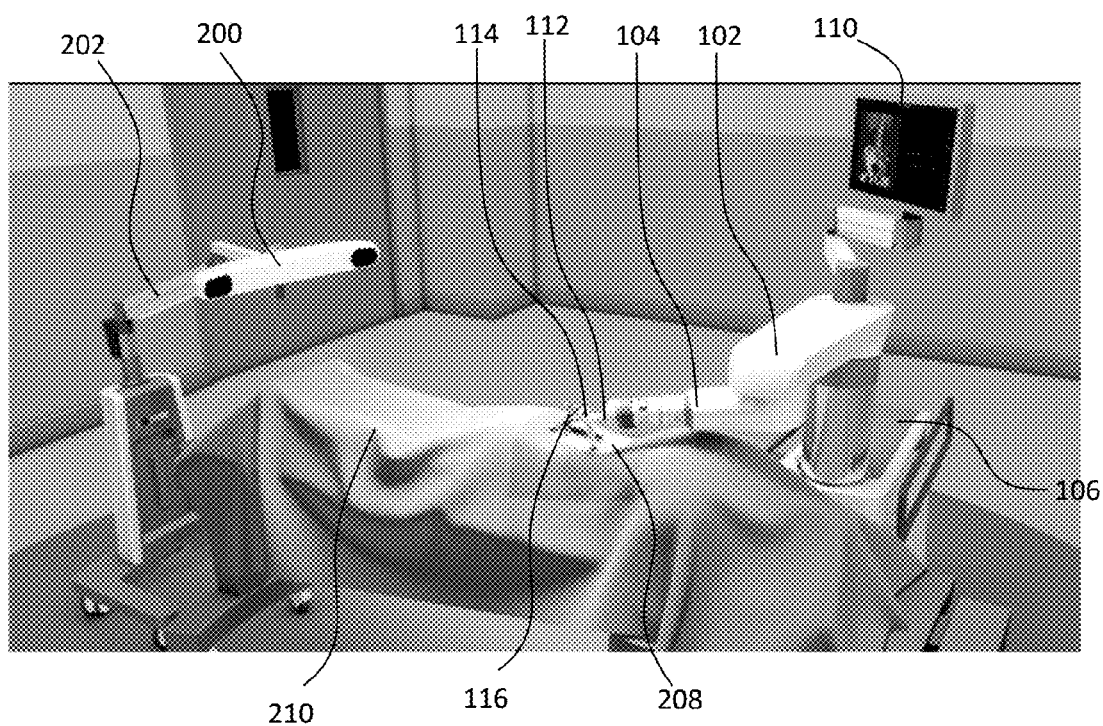
FIG. 2 illustrates the robotic system including positioning of the surgical robot and the camera relative to the patient according to one embodiment.

Turning now to the drawing, FIGS. 1 and 2 illustrate a surgical robot system 100 in accordance with an exemplary embodiment. Surgical robot system 100 may include, for example, a surgical robot 102, one or more robot arms 104, a base 106, a display 110, an end-effector 112, for example, including a guide tube 114, and one or more tracking markers 118. The surgical robot system 100 may include a patient tracking device 116 also including one or more tracking markers 118, which is adapted to be secured directly to the patient 210 (e.g., to the bone of the patient 210). The surgical robot system 100 may also utilize a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 in a given measurement volume viewable from the perspective of the camera 200. The camera 200 may scan the given measurement volume and detect the light that comes from the markers 118 in order to identify and determine the position of the markers 118 in three-dimensions. For example, active markers 118 may include infrared-emitting markers that are activated by an electrical signal (e.g., infrared light emitting diodes (LEDs)), and passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End-effector 112 may be coupled to the robot arm 104 and controlled by at least one motor. In exemplary embodiments, end-effector 112 can comprise a guide tube 114, which is able to receive and orient a surgical instrument 608 (described further herein) used to perform surgery on the patient 210. As used herein, the term "end-effector" is used interchangeably with the terms "end-effectuator" and "effectuator element." Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively controlled). In some exemplary embodiments, selective control of the translation and orientation of end-effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end-effector 112 and/or the surgical instrument 608. Thus, in use, in exemplary embodiments, a physician or other user can operate the system 100, and has the option to stop, modify, or manually control the autonomous movement of end-effector 112 and/or the surgical instrument 608. Further details of surgical robot system 100 including the control and movement of a surgical instrument 608 by surgical robot 102 can be found in co-pending U.S. patent application Ser. No. 13/924,505, which is incorporated herein by reference in its entirety.

The robotic surgical system 100 can comprise one or more tracking markers 118 configured to track the movement of robot arm 104, end-effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, or on the end-effector 112. In exemplary embodiments, at least one tracking marker 118 of the plurality of tracking markers 118 can be mounted or otherwise secured to the end-effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screw driver, dilator, implant inserter, or the like). Thus, the tracking markers 118 enable each of the marked objects (e.g., the end-effector 112, the patient 210, and the surgical tools 608) to be tracked by the robot 102. In exemplary embodiments, system 100 can use tracking information collected from each of the marked objects to calculate the orientation and location, for example, of the end-effector 112, the surgical instrument 608 (e.g., positioned in the tube 114 of the end-effector 112), and the relative position of the patient 210.

In exemplary embodiments, one or more of markers 118 may be optical markers. In some embodiments, the positioning of one or more tracking markers 118 on end-effector 112 can maximize the accuracy of the positional measurements by serving to check or verify the position of end-effector 112. Further details of surgical robot system 100 including the control, movement and tracking of surgical robot 102 and of a surgical instrument 608 can be found in co-pending U.S. patent application Ser. No. 13/924,505, which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end-effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end-effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
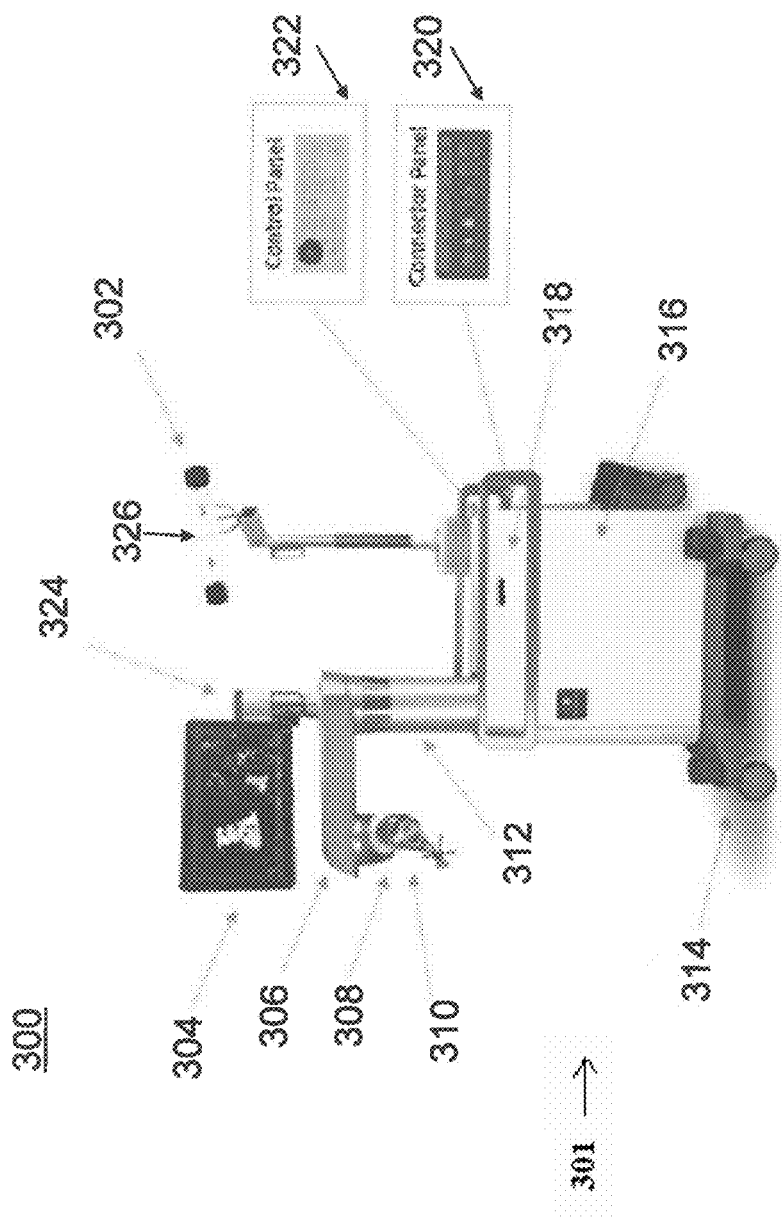
FIG. 3 illustrates a surgical robotic system in accordance with an exemplary embodiment.

Similar to surgical robot system 100, FIG. 3 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end-effector 310, vertical column 312, casters 314, cabinet 316, tablet drawer 318, connector panel 320, control panel 322, and ring of information 324. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 1 and 2.

Figure 4:
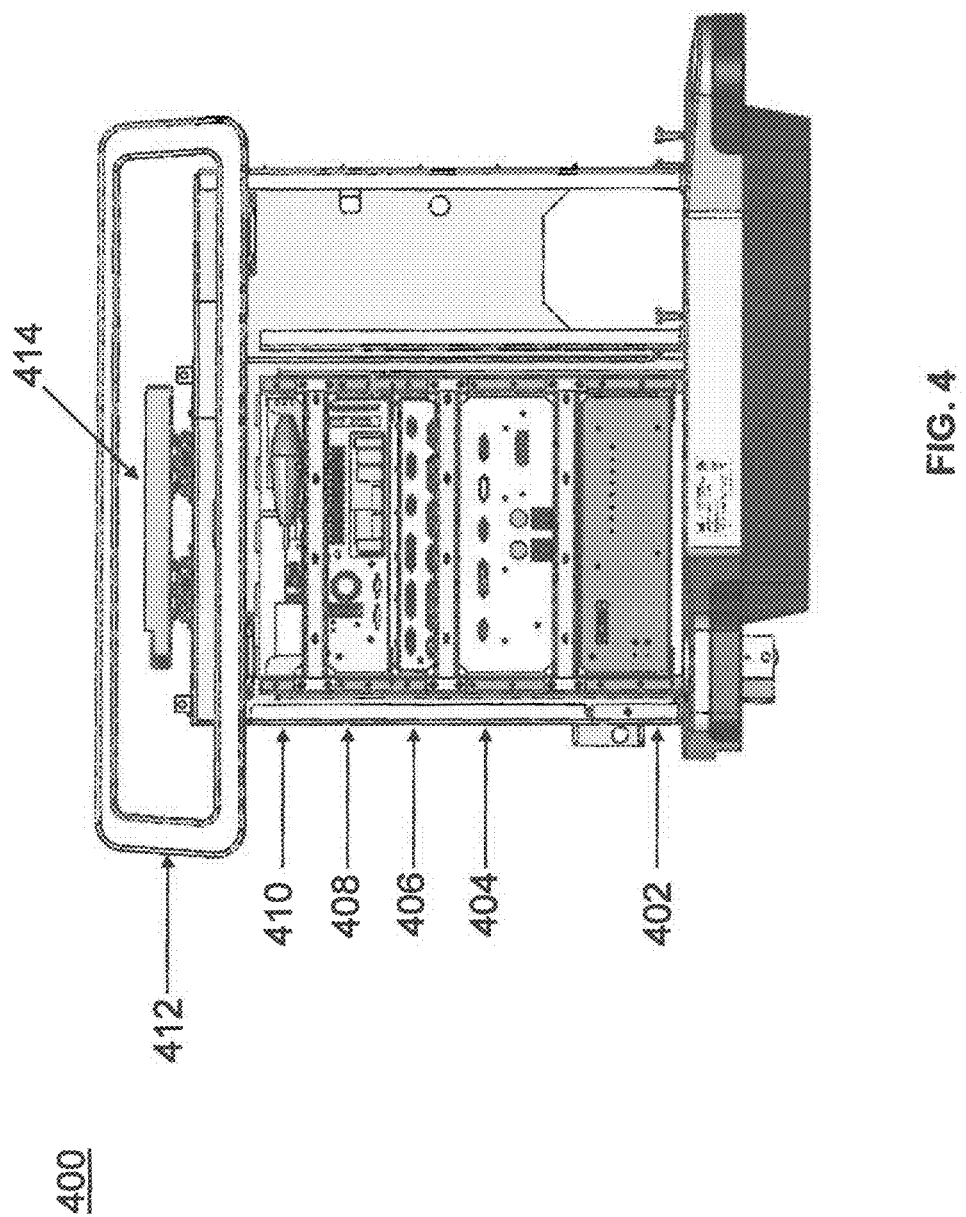
FIG. 4 illustrates a portion of a surgical robot in accordance with an exemplary embodiment.

FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
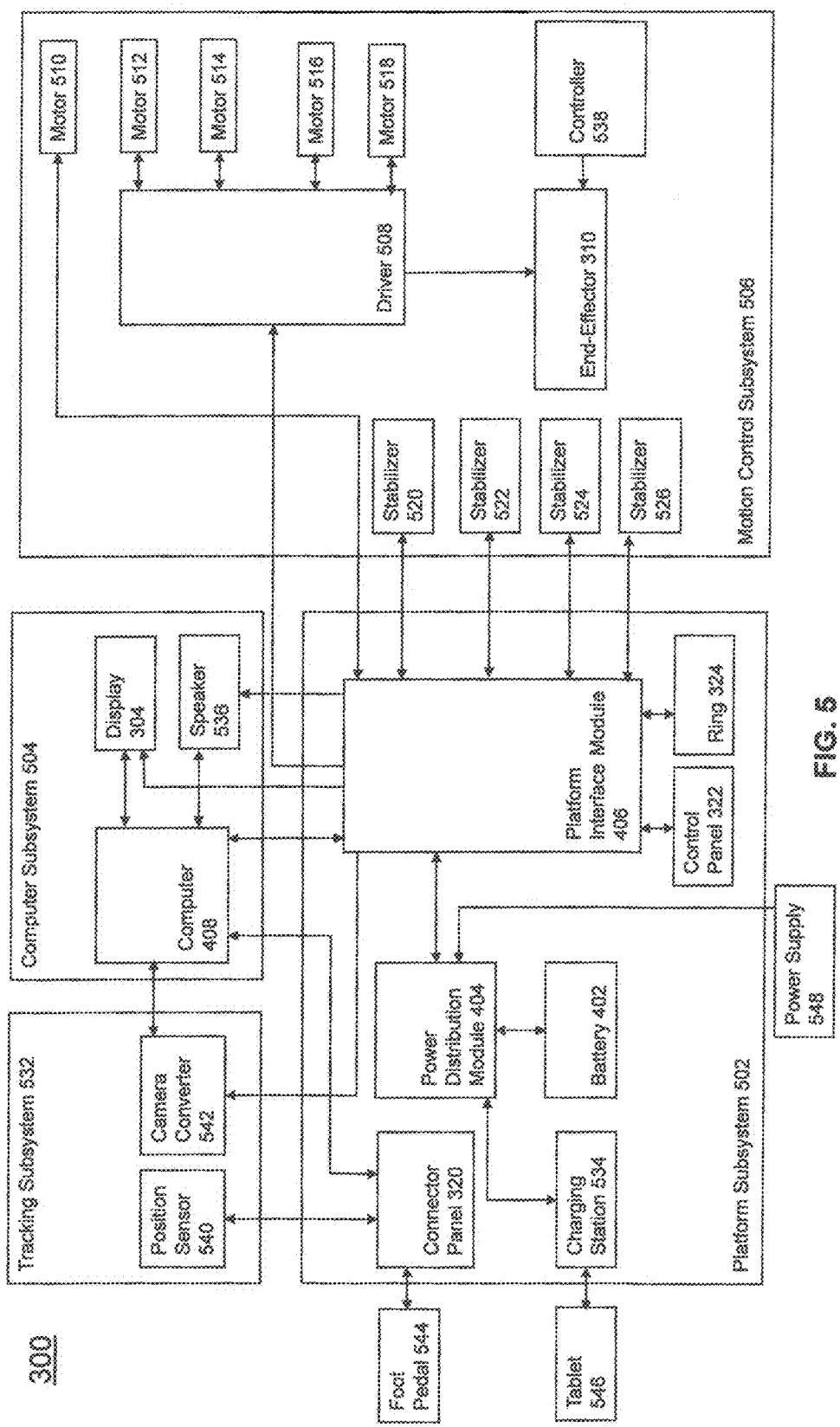
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end-effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end-effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein.

Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure.

Motion control subsystem 506 may be configured to physically move vertical column 312, upper arm 306, lower arm 308, or rotate end-effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end-effector 310 in a manner such that one may control the roll and one may control the tilt, thereby providing multiple angles that end-effector 310 may be moved. These movements may be achieved by controller 538 which may control these movements through load cells disposed on end-effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on three dimensional image of the patient's anatomy on display 304. The user may initiate this automatic movement by stepping on foot pedal 544 or some other input means.

FIG. 6 illustrates a surgical robot system 600 consistent with an exemplary embodiment. Surgical robot system 600 may comprise end-effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end-effector 602 so that surgical robot system 600 may assist a user (for example, a surgeon) in operating on the patient 210. Surgical robot system 600 may be consistent with previously described surgical robot system 100 and 300.

Figure 8:
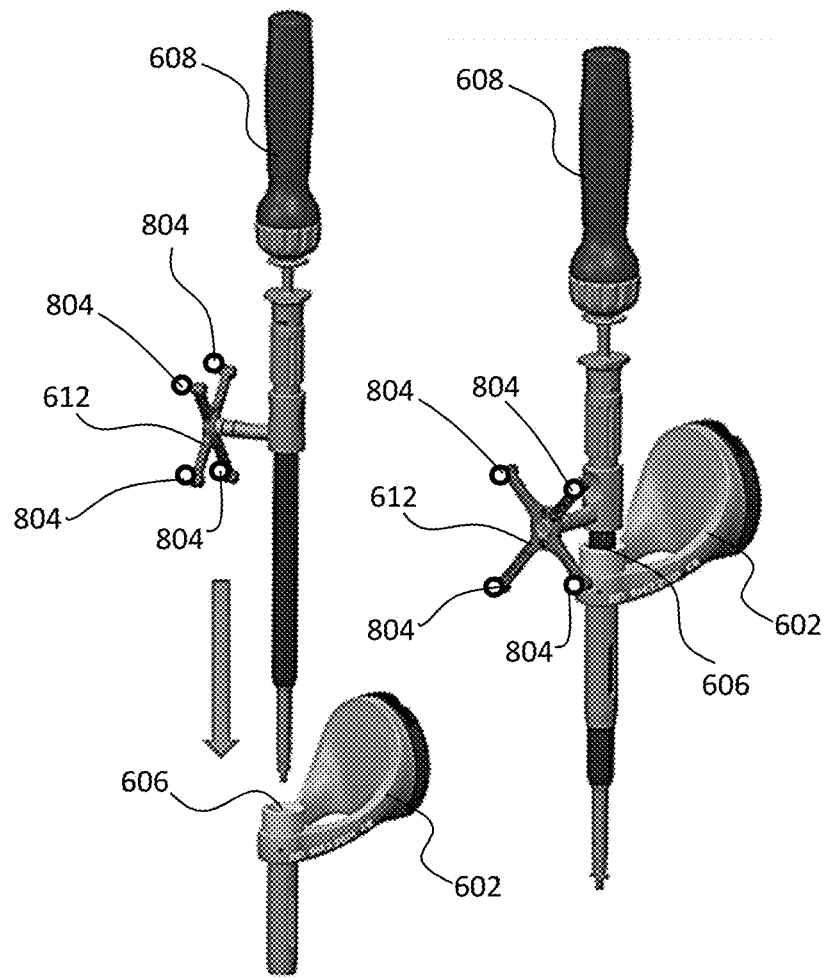
FIG. 8 illustrates a surgical instrument and the end-effector, before and after, inserting the surgical instrument into the guide tube of the end-effector according to one embodiment.

A tracking array 612 may be mounted on instrument 608 to monitor the location and orientation of instrument tool 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end-effector 602, and/or the patient 210. The tracking devices may be consistent with those structures described in connection with camera stand 302 and tracking subsystem 532.

Figure 7A:
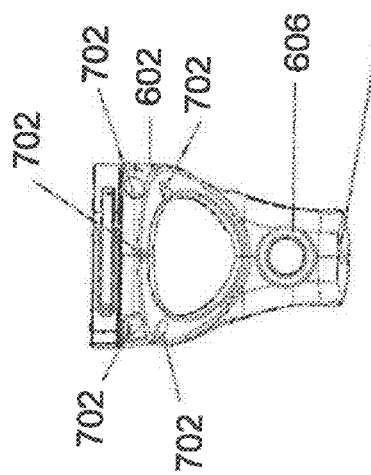
FIGS. 7A-7C illustrate an end-effector in accordance with an exemplary embodiment.
Figure 7B:
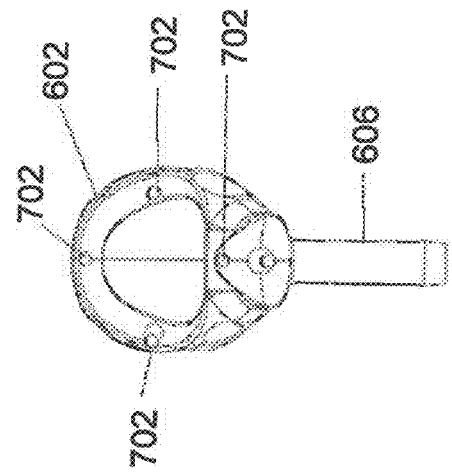
Figure 7C:
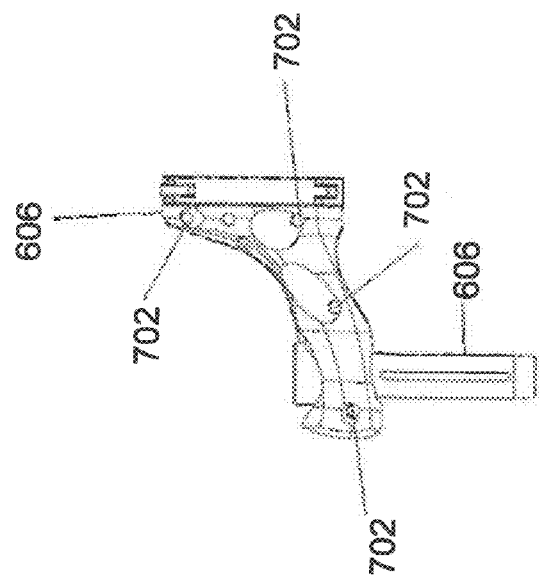

FIGS. 7A, 7B, and 7C illustrate a top view, front view, and side view, respectively, of end-effector 602 consistent with an exemplary embodiment. End-effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end-effector 602 may be controlled by the system 100, 300, 600, and when the markers 702 are deactivated, the end-effector 602 may be locked in position and unable to be moved by the system 100, 300, 600.

Markers 702 may be disposed on or within end-effector 602 in a manner such that the markers 702 are visible by one or more cameras 200, 326 or other tracking devices associated with the surgical robot system 100, 300, 600. The camera 200, 326 or other tracking devices may track end-effector 602 as it moves to different positions and viewing angles by following the movement of tracking markers 702. The location of markers 702 and/or end-effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end-effector 602 is in a desirable position in relation to robot arm 604, robot base 610, the patient 210, and/or the user.

For example, as shown in FIG. 7A, markers 702 may be placed around the surface of end-effector 602 so that a tracking device placed away from the surgical field 208 and facing toward the robot 102, 301 and the camera 200, 326 is able to view at least 3 of the markers 702 through a range of common orientations of the end-effector 602 relative to the tracking device 100, 300, 600. For example, distribution of markers 702 in this way allows end-effector 602 to be monitored by the tracking devices when end-effector 602 is translated and rotated in the surgical field 208.

In addition, in exemplary embodiments, end-effector 602 may be equipped with infrared (IR) receivers that can detect when an external camera 200, 326 is getting ready to read markers 702. Upon this detection, end-effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end-effector 602 and adjust the instrument 608 is evident in FIG. 8. The hollow tube or guide tube 114, 606 of the end-effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screw driver is exemplified as the surgical tool 608, it will be appreciated that any suitable surgical tool 608 may be positioned by the end-effector 602. By way of example, the surgical instrument 608 may include one or more of a guide wire, cannula, a retractor, a drill, a reamer, a screw driver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

Figure 9:
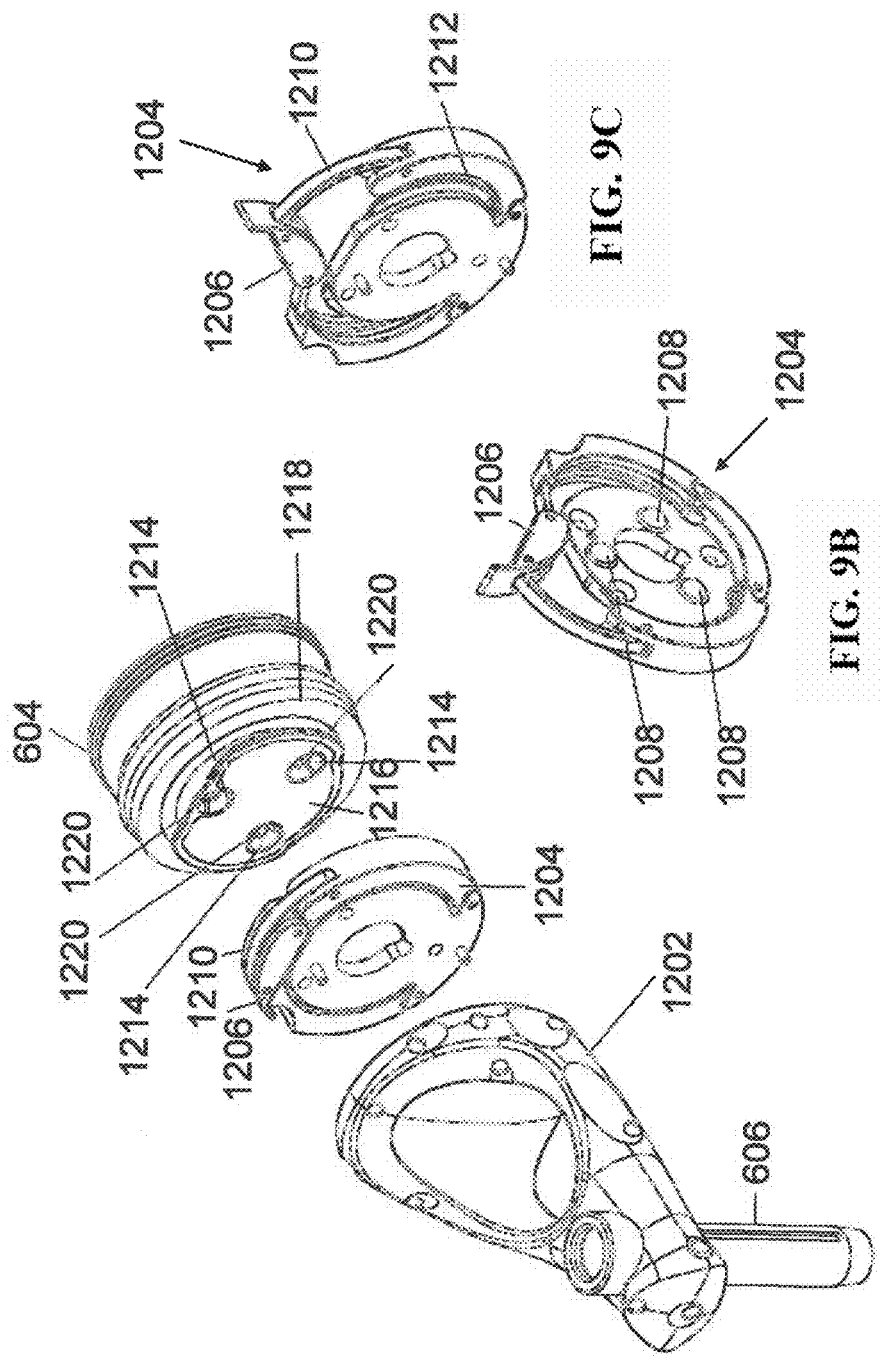
FIGS. 9A-9C illustrate portions of an end-effector and robot arm in accordance with an exemplary embodiment.

FIGS. 9A-9C illustrate end-effector 602 and a portion of robot arm 604 consistent with an exemplary embodiment. End-effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220.

End-effector 602 may mechanically interface and/or engage with the surgical robot system and robot arm 604 through one or more couplings. For example, end-effector 602 may engage with robot arm 604 through a locating coupling and/or a reinforcing coupling. Through these couplings, end-effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end-effector 602 regardless of the orientation of end-effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end-effector 602 to robot arm 604 as lip 1212 and lip 1218 engage clamp 1204 in a manner to secure end-effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end-effector 602 may be robustly secured to robot arm 604.

Spring 1210 may be a curved beam in tension. Spring 1210 may be comprised of a material that exhibits high stiffness and high yield strain such as virgin PEEK (polyether-ether-ketone). The linkage between end-effector 602 and robot arm 604 may provide for a sterile barrier between end-effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end-effector 602 and/or robot arm 604 that slips over an interface between end-effector 602 and robot arm 604 and tightens with a screw mechanism, an over center linkage, or a cam mechanism.

Figure 10:
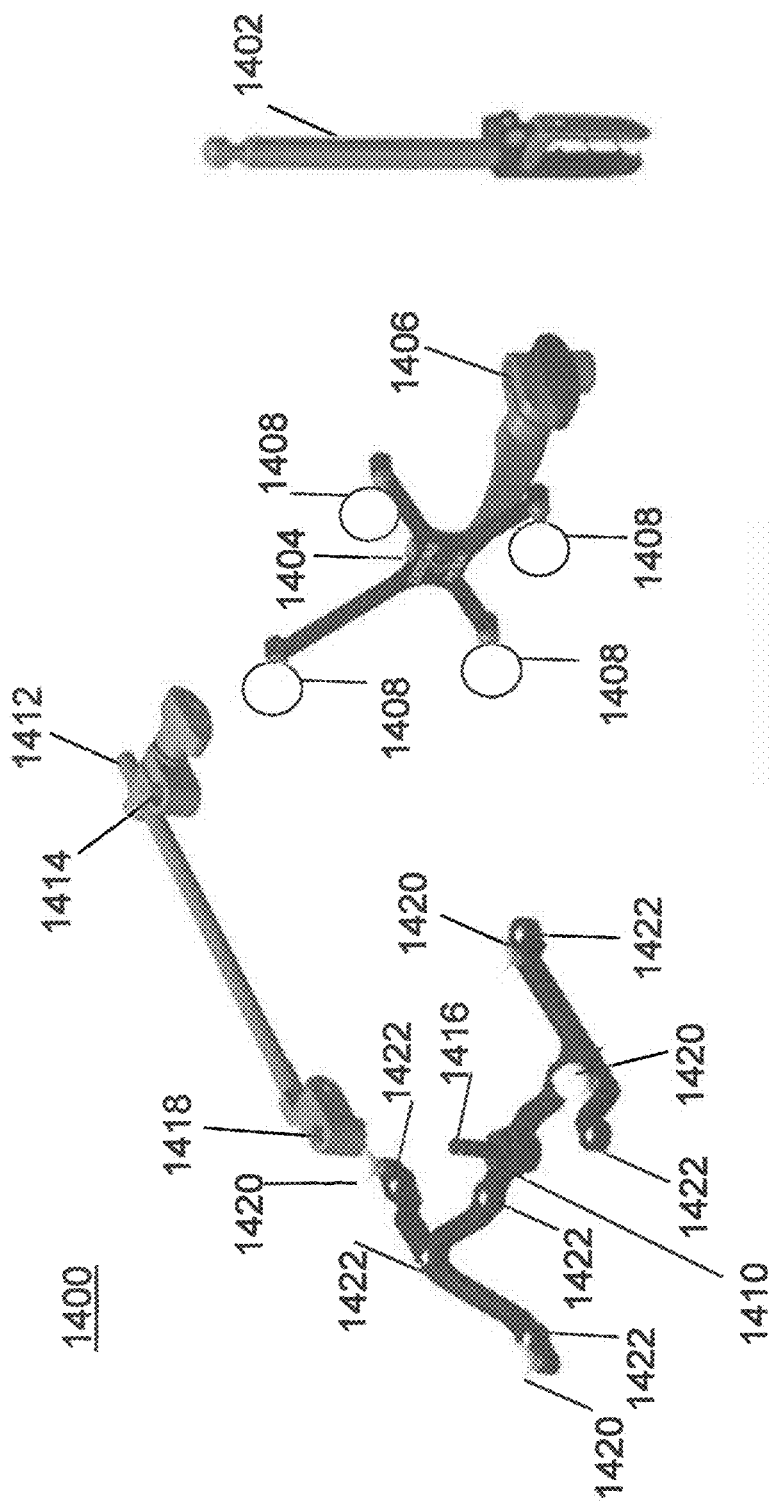
FIG. 10 illustrates a dynamic reference array, an imaging array, and other components in accordance with an exemplary embodiment.
Figure 11:
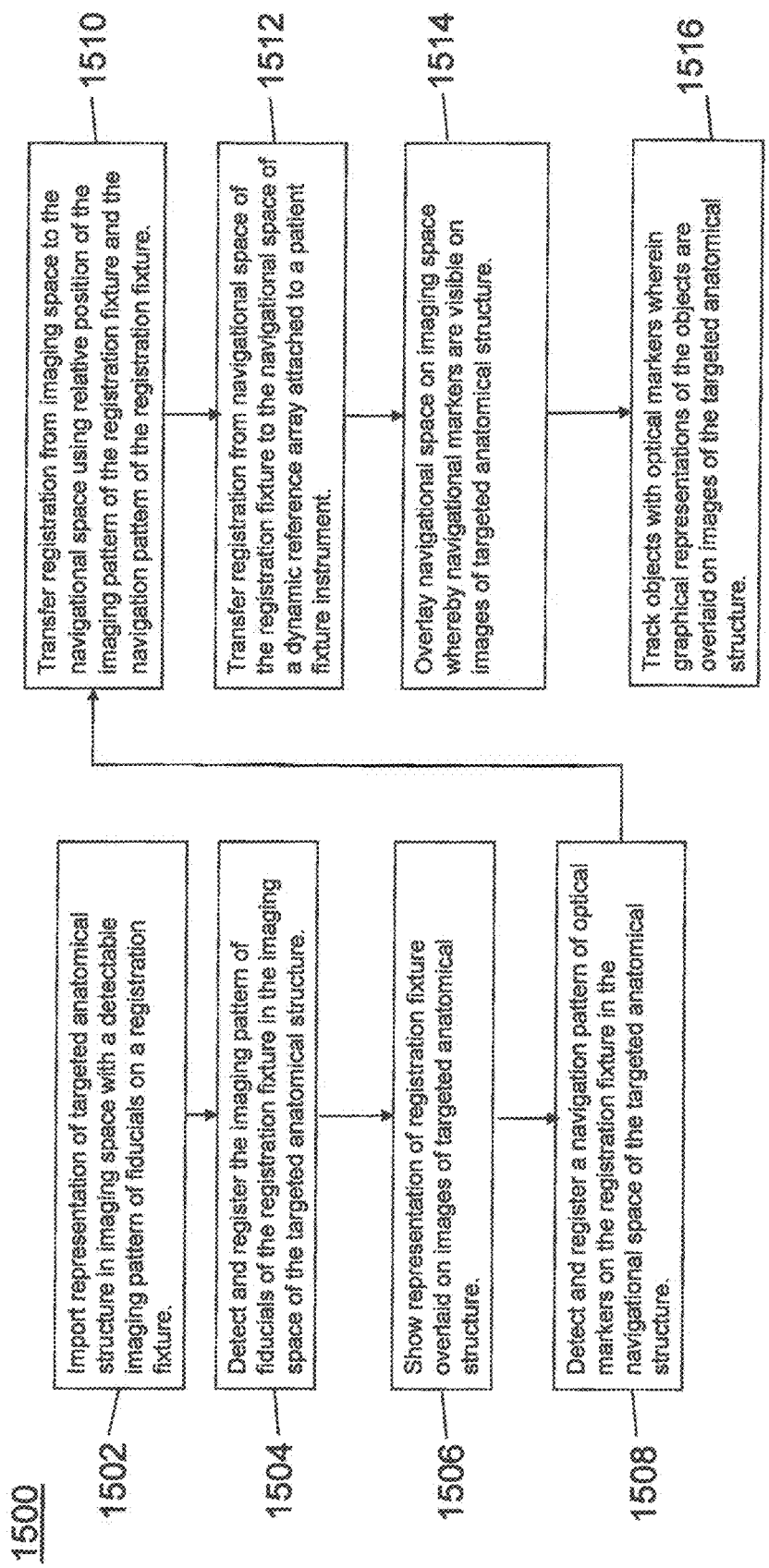
FIG. 11 illustrates a method of registration in accordance with an exemplary embodiment.

Referring to FIGS. 10 and 11, prior to or during a surgical procedure, certain registration procedures may be conducted in order to track objects and a target anatomical structure of the patient 210 both in a navigation space and an image space. In order to conduct such registration, a registration system 1400 may be used as illustrated in FIG. 10.

In order to track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 11 provides an exemplary method 1500 for registration consistent with the present disclosure. Method 1500 begins at step 1502 wherein a graphical representation (or image(s)) of the targeted anatomical structure may be imported into system 100, 300 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

Figure 12A:
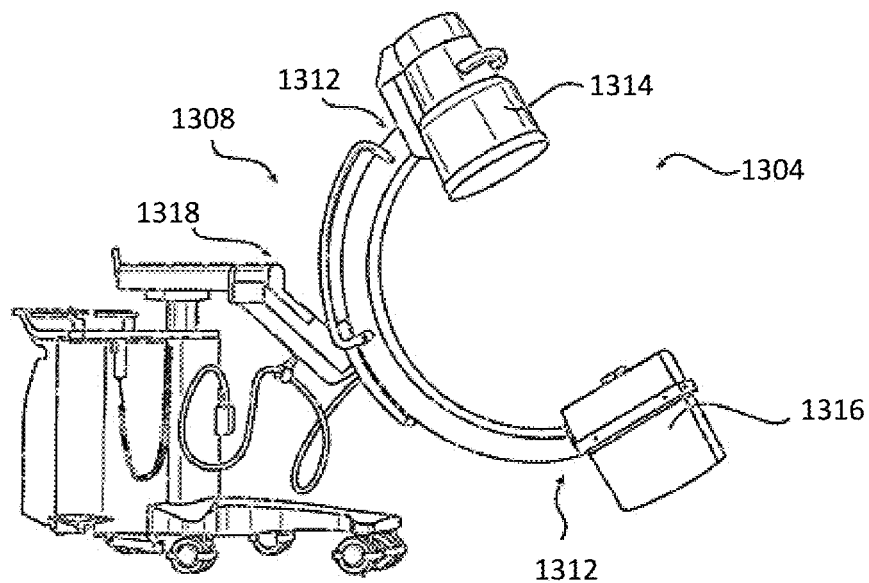
FIG. 12A-12B illustrate embodiments of imaging devices according to exemplary embodiments.
Figure 12B:
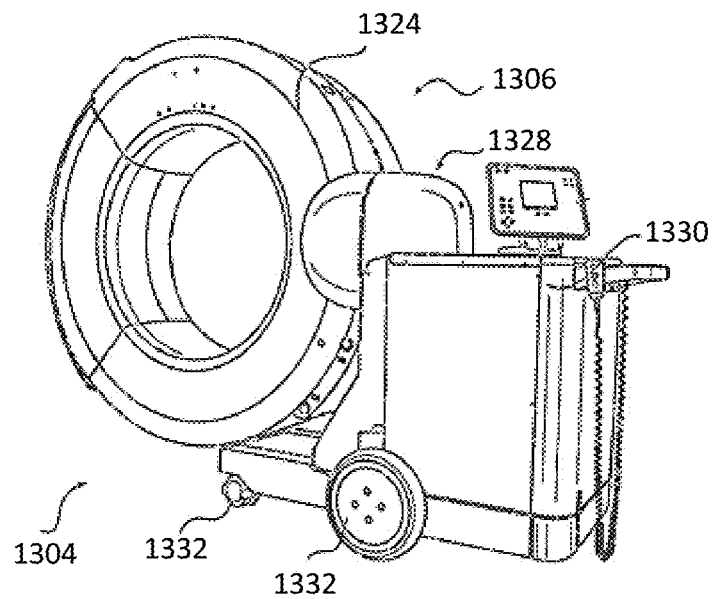

FIGS. 12A-12B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Turning now to FIGS. 13-19, sensor-controlled and/or omni-directional movement of the robot system is described. In particular, various embodiments may provide controlled movement of the system, for example, in any X-Y direction with Wag-rotation about any Z-axis using omni-directional wheels 62, 64.

Figure 13:
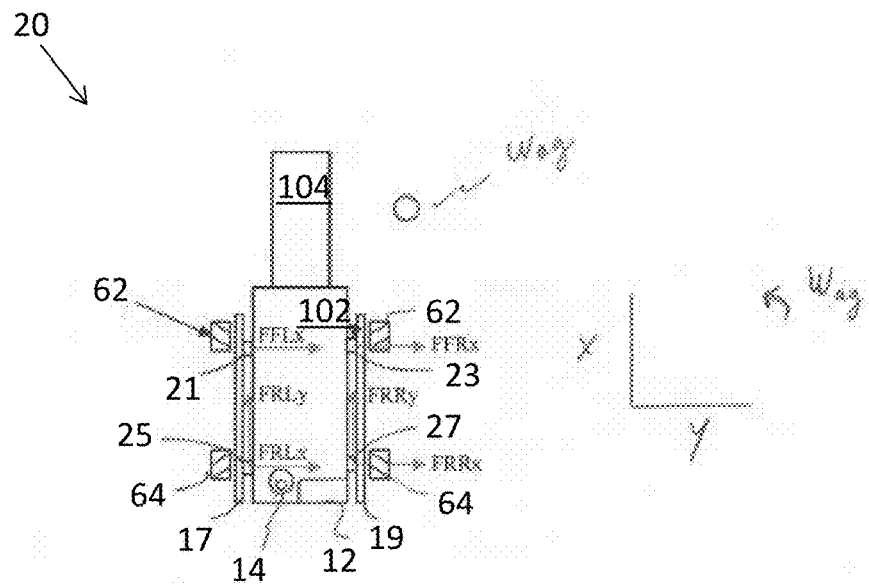
FIG. 13 is a top plan view of a robot device equipped with the control system and omni-directional wheels ("omni-wheels") of the present disclosure and depicting a first example of an array of sensors.

With reference to FIG. 13, one embodiment of a control system 20 for sensor-controlled movement of the robot system is shown. As described earlier, the control system 20 may include computer subsystem 504, motion control subsystem 506. Input devices may include a display 110 with touch screen capabilities, a keyboard with function keys 12, handles 17, 19, a joystick 14, or the like. Any of these input devices may control either or both of the motion control portion 506 and the computer subsystem 504. Switching between a motion control mode and a robot control mode may be accomplished by a function key, a touch screen command from one of the display devices, or other desired method. The robot system may also include, as part of the motion control portion 506 and/or computer subsystem 504, a smart phone or cellular phone link or global positioning system (GPS) that may be useful for communicating information concerning a position of the patient or the robot system.

Control system 20 of FIG. 13 is depicted as a plan view of the robot system, depicting a top view of the surgical robot 102 and the robot arm 104. Omni-wheels 62, 64 are separated into front portion omni-wheels 62, left and right, and rear portion omni-wheels 64, also left and right. FIG. 13 also depicts the three axes for the three degrees of omni-wheel freedom of motion of the system. As depicted in the figure, these include freedom to move left or right along a y-axis, freedom to move forward and backward along an x-axis, and freedom of rotation along a rotational axis Wag that is perpendicular to a plane formed by the x and y axes, i.e., a vertical axis. Thus, the vertical axis Wag in FIG. 13 is perpendicular to the plane of the drawing.

FIG. 13 may also provide a useful reference for a discussion of the sensors used in this disclosure. Left sensors 21, 25 are mounted on the left handle 17 while right sensors 23 and 27 are mounted on the right handle 19. A first embodiment may include these four sensors 21, 23, 25, 27, as shown. A person, such as a health care professional operating the robot system 100, may position the device by using the handles 17, 19 and the motion control portion 504.

In one embodiment, the motion control may have two modes, a transport mode and a fine-tune mode. For example, if the robot system 100 is transported from one wing of a hospital or other health-care facility, speed may be more highly valued than fine-tuned positioning. Thus, pushing on the rear portion handles 17, 19 of system 100 may activate the transport mode. Pushing on either of the two handles 17, 19 may activate a fine-tune mode, in which every movement of the omni-wheels 62, 64 is slower and more deliberate. Switching between these modes may also be accomplished by appropriate programming allowing the user to switch via a function key, a command, a touch-screen input, and so forth.

In fine tune mode, motion control 504 may be used to return the robot system 100 to a set position, e.g., reset to a predetermined position. For example, and with reference to FIG. 3, if a surgical procedure has concluded, the user may wish to move the robot system 100 to a preset configuration. The position may be programmed into the motion control 504. This may be accomplished using the keyboard or function buttons 12 available to the operator, the touch screens of the display devices 110, a joystick 14 or a predetermined applied force and direction to the handles 17, 19. The keyboard, the function buttons and the touch screen display devices may also be used to control the robot functions and motion control portions, including movement of the omni-directional wheels 62, 64.

The capabilities of the omni-wheels 62, 64 may also be used so that the system moves about a specified axis. This may be any convenient axis, such as a geometrical center of the robot 100, a particular feature or part of the robot system 100 or its base 106, a feature of the robot, such as the end-effector 112 mounted thereon, and so forth. The motion applied by the omni-wheels 62, 64 may also be proportional to the force(s) applied to the sensor(s) 21, 23, 25, 27—a light force may result in slower, more deliberate speed while a higher force or heavier touch may result in higher speeds applied by the omni-wheels 62, 64. In addition, the direction in which the forces are applied may indicate the desired direction of movement of robot system 100. The forces applied to the sensor(s) 21, 23, 25, 27 may be resolved by motion control 504 into a resultant vector and moment that is used to drive each of front wheels 62 and rear wheels 64, as needed, to provide the desired motion.

We now discuss examples of movement using FIG. 13. In one example, pushing the left handle 17 forward would operate to cause the device to go forward and turn the device to the right. In another example, pushing the left handle 17 activates sensors 21, 25 to require forward movement. The sensor(s) 21, 23, 25, 27 may be strain gauges that interpret the force as applied in a particular direction for sensors 21, 25, forward, but with no force applied to sensors 23, 27. Since no force is applied to the right handle 19 and its sensors 23, 27, motion control 504 interprets the signals from the sensors 23, 27 as calling for a right turn with only a slight forward motion. Thus, the robot 100 makes a tight turn to the right with minimal forward movement via the omni-wheels 62, 64. In embodiments, all four wheels 62, 64 may move in this example to achieve a slight rightward turn movement. The wheels 62, 64 may be controlled individually so that their movements together achieve a desired movement of the robot base 106. As discussed above, this is an example of movement in a fine-tune mode. In other embodiments, only the left wheels 62, 64 may be activated or only the right wheels 62, 64, depending on the desired movement.

In another example, pushing left handle 17 to the right applies a force to sensors 21, 25, calling for rightward lateral or side movement. If no forward or backward force is applied to the sensors 21, 25 and no force is applied to right sensors 23, 27, motion control 504 interprets the signals as calling for rightward lateral movement with no forward or backward motion, still in a fine-tune mode. Accordingly, all four omni-wheels 62, 64 may make a small movement in the direction indicated, i.e., a few mm or inches to the right. In another example, the front wheels 62 may turn in a forward and leftward direction while the rear wheels 64 turn backwards and to the right to achieve a left turn or rotation in position. In another example, pushing both handles 17, 19 to the left will bring up a transport mode rather than a fine-movement mode. This may cause the robot 100 to move to the left to a leftward position. The same may be said for pushing both handles 17, 19 forward, in an x-axis direction, to move the base 106 forward, now in a transport mode rather than in a fine-tune mode. Although described with reference to applying a force to specific handles 17, 19 and sensors 21, 23, 25, 27, it will be appreciated that more or less handles and/or sensors may be employed with the system. In addition, different forces and/or movements may occur in a number of different configurations in order to employ the fine-tune and/or transport modes and/or to move the robot system 100 about the operating room. It is also envisioned that these types of sensors, omni-wheels, and movement controls may be applied to other equipment in the operating room environment including the camera stand 202, carts, imaging devices, or other heavy machinery or operating room equipment.

The sensors 21, 23, 25, 27 used in embodiments of the present disclosure may include one or more force sensors. These include strain gauges, force-sensing resistors, piezoelectric sensors, piezocapacitive pressure sensors, piezoresistors and microelectro-mechanical systems (MEMS) micro-scale strain gauges. Typically, a force sensor possesses an electrical property that is changed when a user applies a force to the sensor. The property may be an electrical conductance, a resistance or a capacitance that increases or decreases in a predictable manner when a force is applied. Piezo-type sensors may generate a small microvoltage when a pressure is applied. The sensor may be part of an electrical circuit for detecting such a change, e.g., a Wheatstone bridge. By using an array or plurality of strain gauges or sensors, the user may fine-tune the direction of the desired force to be applied to the omni-wheels.

Figure 15A:
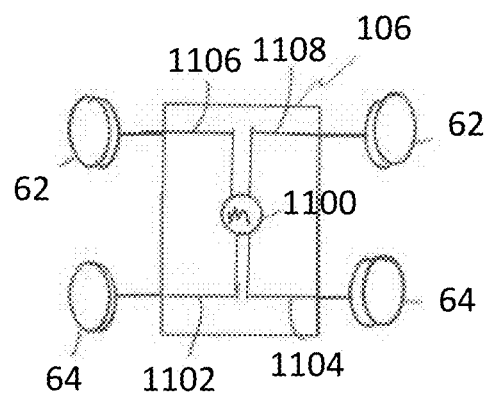
FIGS. 15A and 15B depict configurations for applying power to the omni-wheels of the robot.
Figure 15B:
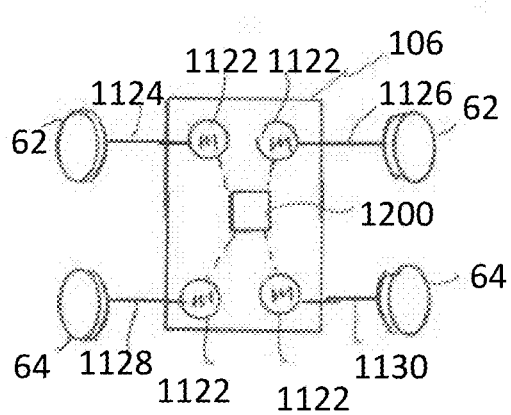

The sensors 21, 23, 25, 27 used in FIG. 13 and in the examples below may be used to control the wheels 62, 64 of the robot system 100. Examples of such techniques are depicted in FIGS. 15A and 15B. In FIG. 15A, the base 106 of the robot system 100 is depicted with front wheels 62 and rear wheels 64, which may be the same or may be different. In this embodiment, motor 1100 under the direction of the motion control 504, transmits power to each of the wheels 62, 64 as desired. The power supplied to the wheels 62, 64 may include manual operation, automatic operation, or a combination of both. The motor 1100 may have more than one shaft to supply power to axles 1102, 1104, 1106, 1108 to individually power the omni-wheels 62, 64. This allows for fine control of each wheel 62, 64 for precise placement of the base 106 and the robot equipment mounted thereon. In one embodiment, the motor 1100 and each shaft or axle 1102, 1104, 1106, 1108 may further comprise a rotary encoder or other feedback mechanism to provide positional feedback to the motion control module.

Alternatively, as depicted in FIG. 15B, base 106 may include a local controller 1120 for allocating power via separate motors 1122 that power independent axles 1124, 1126, 1128, 1130 to each of the omni-wheels 62, 64. It may be simpler for motion control 504 to maintain separate control of each omni-wheels 62, 64 via its own motor. In this embodiment, each motor 1122 may include its own encoder for positional feedback, and may also include an encoder or other feedback mechanism on axles 1124, 1126, 1128, 1130. Other methods for supplying power to the wheels 62, 64 may be used. The local controller or the motion control module may contain a computer program that resolves sensor readings into commands to each of the motors 1122 and axles 1124, 1126, 1128, 1130. With this technique, the omni-directional wheels 62, 64 are individually controlled for very accurate movement by the sensors provided. Feedback from the motion, such as from the rotary encoders on the axles 1124, 1126, 1128, 1130, or by other devices, can be used to store given positions for later use in restoring the base 106 to a desired location.

The sensors 21, 23, 25, 27 used to sense a desired direction of the robot 100 may be mounted in the handles 17, 19, as disclosed above. The sensors 21, 23, 25, 27 may alternatively be mounted in a joystick or in other types of handles, as disclosed in FIGS. 14A-14D. A first alternate embodiment is disclosed in FIG. 14A. In this control system 1610, a plurality of force sensors 1612, six sensors, are mounted in a circular arrangement. A user presses on a surface of the control system, activating the sensors 1612 to guide the robot system 100 in the appropriate direction. The direction is determined by the sensors 1612 that are activated and by the amount of force or pressure applied by the user. This is the same principle used in the example above of the handles 17, 19 of the robot 100. The circular control arrangement is useful for guiding the device in all x-y directions, in a plane. Rotation about a predetermined axis may also be achieved by pushing up or down on the joystick or by commands to the keyboard or function button inputs. For example, depressing the joystick for a few seconds may command the system to rotate clockwise about the axis, while pulling upwardly for a few seconds may command a counter-clockwise rotation.

Figures 14A, 14B, 14C, 14D:
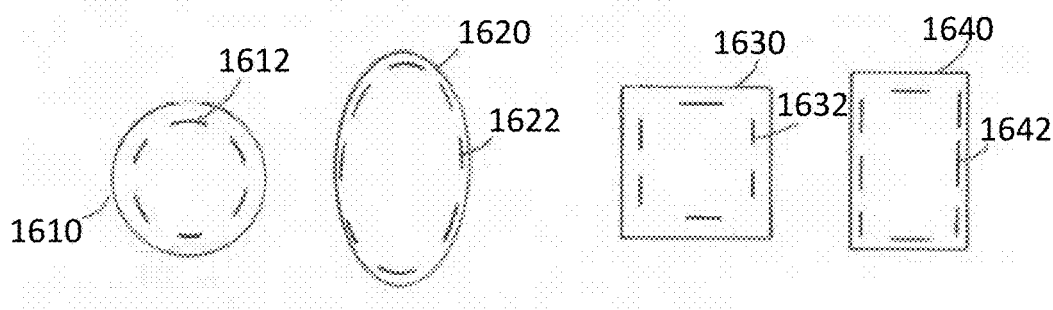
FIGS. 14A-14D depict arrays of sensors useful in moving the robot.

Other examples with similar modes of operation are depicted in FIGS. 14B-14D. In FIG. 14B, eight sensors 1622 are arranged elliptically for a control system 1620 that is more suggestive of forward-backward movement, x-direction, as are the side handles. More sensors 1622 may be used for more sensitivity to the direction desired by the operator. In FIG. 14C, control system 1630 includes six force sensors 1632 mounted in a square pattern as shown, with two sensors 1632 for forward/backward movement and also with additional sensitivity for left/right or sideways direction with a four-corner distribution of the remaining four sensors 1632. FIG. 14D depicts an example of a control system 1640 configured with a plurality of sensors 1642 in a rectangular arrangement. This arrangement includes three sensors 1642 per side, allowing for finer tuning of lateral movements of the robot. Other configurations may be used to guide the robot system 100 and its omni-directional wheels 62, 64.

Figure 16:
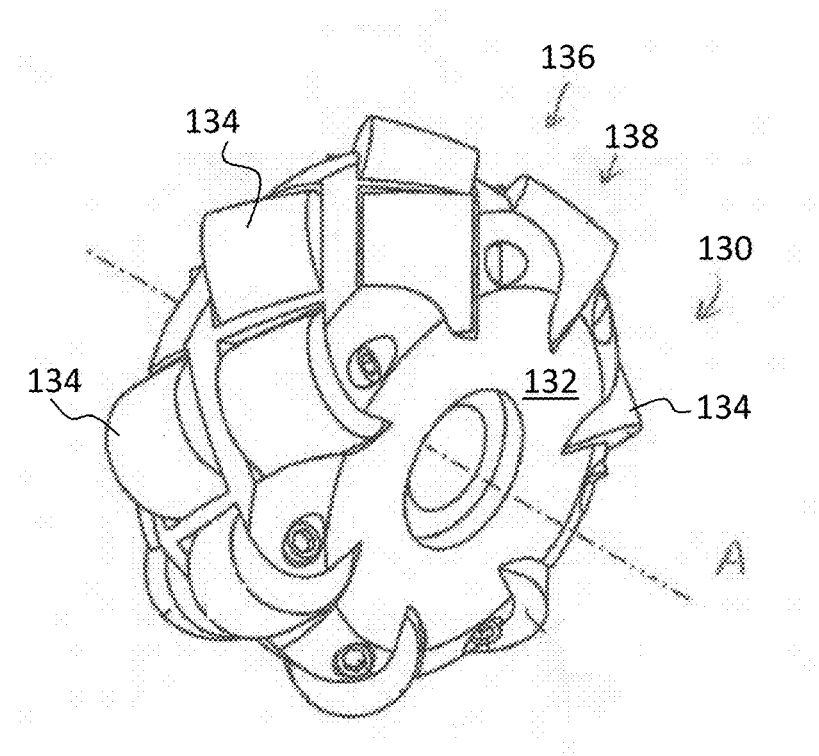
FIG. 16 is a perspective view of an example of a first type of omni-directional wheel ("omni-wheel") useful in imaging systems according to the present disclosure.

There are many types of omni-wheels 62, 64 useful in embodiments of the present disclosure, such as those depicted in FIGS. 16-19. Unlike traditional wheels, which only allow a device to move in one direction (e.g., forward and backward), the omni-directional wheels allow the robot to be moved in every direction (e.g., forward, backward, left, right, diagonally, in an arc, or the like). Thus, the omni-direction wheels 62, 64 allow the robot to be moved in any direction. Omni-directional wheels 62, 64 or Mecanum-type wheels generally have a central hub with a plurality of smaller wheels or rollers on its circumference. The smaller wheels are mounted at an angle to the central axis of the hub, such as 45 degrees or 90 degrees. FIG. 16 depicts an omni-directional wheel 130. This wheel 130 includes a central hub 132 about a central axis A, with a plurality of rollers or wheels 134 mounted in two non-coaxial rows 136, 138 at about a 45-degree angle to the central axis. The wheels or rollers 134 take turns being on the ground, making turning easier. These types of wheels 130 are described in U.S. Pat. Appl. 2010/0187779, which is hereby incorporated by reference in its entirety.

Figure 17:
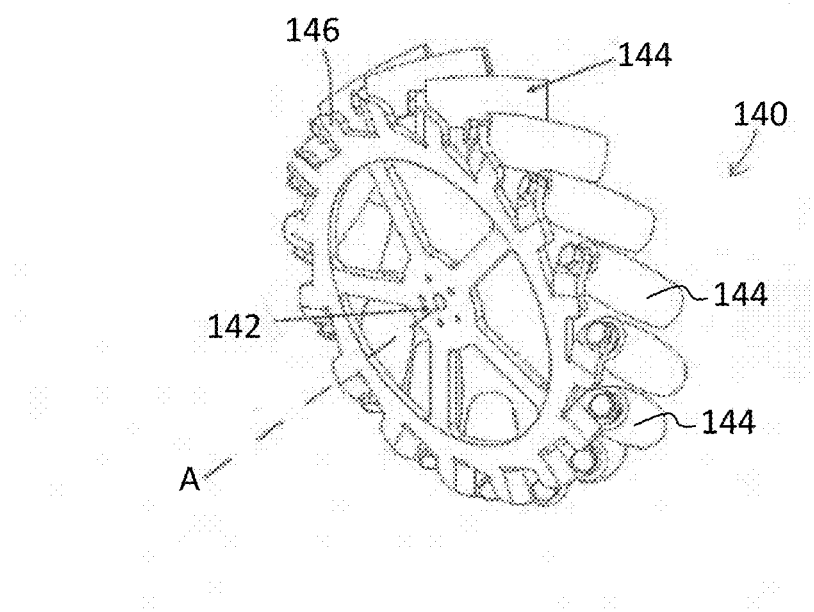
FIG. 17 is a perspective view of an example of a second type of omni-wheel useful in the present disclosure.

Another type of omni-directional wheel 62, 64 useful in the present disclosure is depicted in FIG. 17. Mecanum wheel 140 has a central hub 142 with a central axis A. A plurality of rollers 144 are mounted on flanges 146 on the periphery of the central hub 142. In this example, the flanges 146 are bent at about a 45-degree angle and thus the rollers 144 are also mounted at about a 45-degree angle to the central axis A. Other angles may be used. Each wheel 62, 64 may be powered individually to guide the robot in the desired direction. These types of wheels 140 are described in U.S. Pat. Appl. 2013/0292918, which is hereby incorporated by reference in its entirety.

Figure 18:
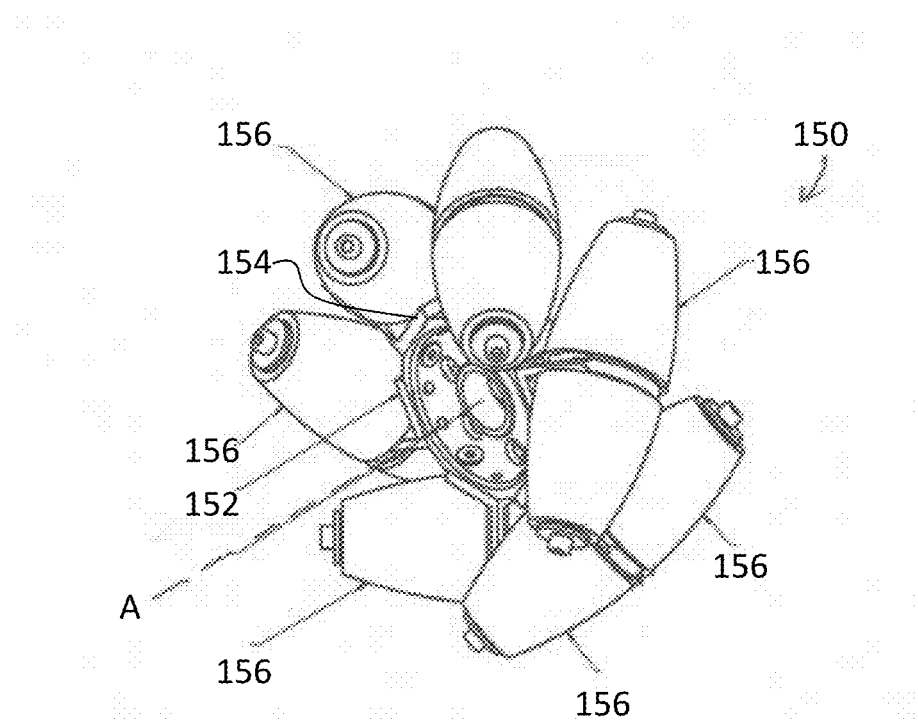
FIG. 18 is a perspective view of an example of a third type of omni-wheel useful in the present disclosure.

FIG. 18 depicts another type of omni-directional wheel 62, 64, a Mecanum wheel 150, useful in the present disclosure. Wheel 150 includes a central hub 152 with a central hub axis A and a plurality of flat circumferential surfaces (not shown). Each surface mounts a protruding spoke 154, which is then used to mount a circumferential roller 156. In this wheel 150, only one or two of the rollers 156 is on the floor or surface at a time, making turning easier. These types of wheels 150 are described in U.S. Pat. No. 8,011,735, which is hereby incorporated by reference in its entirety.

Figure 19:
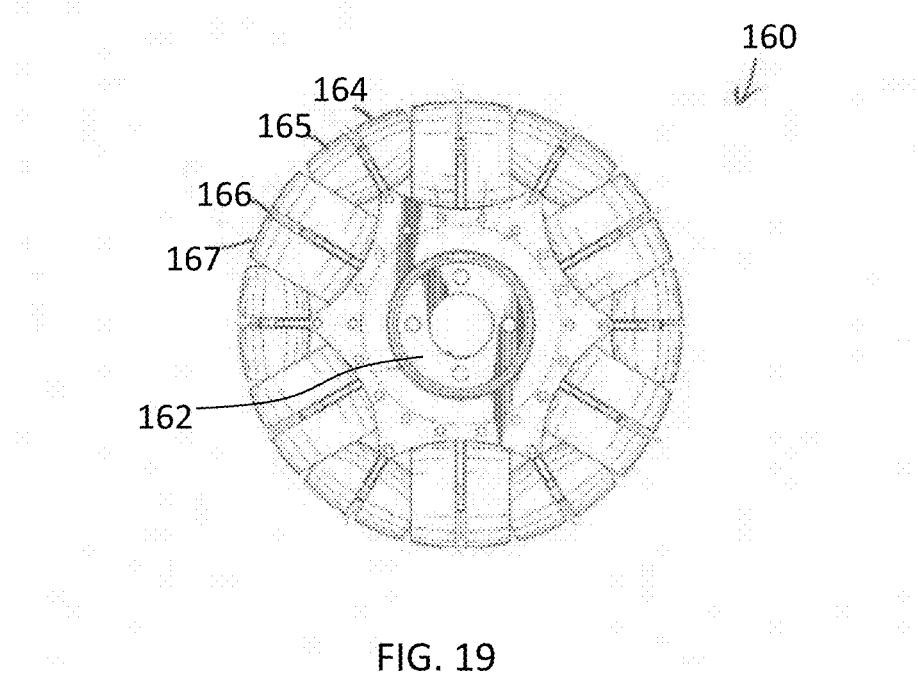
FIG. 19 is an elevational view of an example of a fourth type of omni-wheel useful in the present disclosure.

Yet another type of omni-directional wheel 62, 64, wheel 160 is disclosed in FIG. 19. Wheel 160 includes a central hub 162 which mounts two series of spokes or mounts 164, 166. Each of the first series of spokes 164 mounts a wheel 165 whose axis of rotation is ninety-degrees opposed to a direction of rotation of wheel 160 and central hub 162. Each of the second series of spokes 166 mounts a wheel 167 whose axis of rotation is also ninety-degrees opposed to a direction of rotation of wheel 160. Second series of wheels 167 have a slightly larger diameter than the first series 164 of wheels. Wheel 160 can rotate about an axis (not shown) perpendicular to its central hub 162. Rollers 165, 167 allow the wheels 160 to easily change direction, thus making this a suitable omni-wheel 62, 64. These types of wheels 160 are described in U.S. Pat. Appl. 2015/0130260, which is hereby incorporated by reference in its entirety. Other types of Mecanum or omni-directional wheels 62, 64 may also be used in embodiments of this disclosure.

Once the location of the robot 100 is set in the operating room, the base 106 may be locked into position. For example, the omni-directional wheels 62, 64 may be locked such that they are unable to move. In the alternative, a kickstand or other locking mechanism may be employed to prevent movement of the base 106. Once the locking mechanism is released, the base 106 is again free to move in any direction as described herein.

The advantages of this disclosure include the ability to accurately position large equipment in any desired position or direction, using the three-axis, three-degrees of freedom capabilities described above. The on-board GPS system may also be used to track the position of the equipment and to store and recall positions where the equipment is used. The unique three-axis motion capability of the omni-wheels 62, 64 includes a rotary axis, which may be chosen as desired. By using both motion control and robot control, the operator or diagnostic person can coordinate the position of the system with the patient. The precise positioning made possible by the motion control system, the encoders and the omni-wheels 62, 64 allows the system 100 to have the control and precision of a fixed, non-mobile system.

The motion control system, the sensors, the encoders and the system memory allow the system to act as a smart system. The sensors allow one to position the system as desired using the sensors and the memory. The system includes capabilities for precise, small movements for a particular procedure for a patient, as well as a transport mode, e.g., for moving to another patient or to another room. This allows users to park the system in a more convenient location and then to recall the system to a precise location when desired. The system's memory gives users the ability to quickly and accurately recall the base 106 to a particular position when it is needed later.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. It is further envisioned that features from one embodiment may be combined or used with the features from a different embodiment described herein. Moreover, although specific terms are employed herein, as well as in the claims which follow, they are used only in a generic and descriptive sense, and not for the purposes of limiting the described invention, nor the claims which follow. The entire disclosure of each patent and publication cited herein is incorporated by reference, as if each such patent or publication were individually incorporated by reference herein. Various features and advantages of the invention are set forth in the following claims.

What is claimed is:

1. A surgical robot system comprising:
a robot having a robot base, a robot arm coupled to the robot base, and an end-effector coupled to the robot arm, the end-effector including a plurality of tracking markers detectable by at least one camera;
a plurality of omni-directional wheels affixed to the robot base allowing multiple-axis movement of the robot;
a plurality of sensors for detecting a desired movement of the robot base; and
a control system responsive to the plurality of sensors for controlling the multiple-axis movement of the robot by actuating two or more of the plurality of omni-directional wheels.

2. The surgical robot system of claim 1, wherein each of the plurality of omni-directional wheels includes a central hub with a plurality of rollers mounted to the central hub.

3. The surgical robot system of claim 2, wherein the plurality of rollers are mounted at an angle relative to a central axis of the central hub.

4. The surgical robot system of claim 1, wherein the multiple axis movement is selected from the group consisting of: movement in a plane; movement in a 2-D coordinate system; and three axis movement in a forward-backward direction, movement in a side direction and rotation about a defined axis perpendicular to the forward-backward and side directions.

5. The surgical robot system of claim 1, wherein the plurality of sensors for detecting a desired movement are selected from the group consisting of a strain gauge, force-sensing resistor, a piezoelectric sensor, a piezo capacitive pressure sensor, a piezo resistor and a microelectromechanical systems (MEMS) micro-scale strain gauge.

6. The surgical robot system of claim 1, wherein the plurality of sensors for detecting a desired movement are mounted in left-and-right handles of the robot base.

7. The surgical robot system of claim 1, wherein the plurality of sensors for detecting a desired movement are mounted in a joystick of the robot base, and wherein the desired movement is indicated by a movement of the joystick.

8. The surgical robot system of claim 1, wherein the plurality of sensors are operable to sense a desired front left wheel force in a forward/backward direction, a desired rear left wheel force in the forward/backward direction, a desired rear left wheel force in a side direction, a desired front right wheel force in a forward/backward direction, a rear right wheel force in a side direction and a rear right wheel force in a backward/forward direction.

9. The surgical robot system of claim 1, wherein the plurality of sensors comprises a sensor array mounted in a planar configuration selected from the group consisting of a generally circular array, a generally elliptical array, a generally rectangular array and a generally square array.

10. The surgical robot system of claim 1, further comprising at least one motor under control of the control system for providing power to each of the plurality of omni-directional wheels.

11. The surgical robot system of claim 1, wherein the plurality of tracking markers in the end-effector are active markers having an active state and an inactive state, the active state emitting an infrared signal detected by the at least one camera, and the inactive state not emitting the infrared signal such that the plurality tracking markers are not detected by the at least one camera.

12. The surgical robot system of claim 1, further comprising a surgical instrument having one or more tracking markers to be tracked by the robot system, the surgical instrument configured to be positioned in the end-effector in order to align the surgical instrument along a given trajectory for a surgical procedure.

13. A surgical robot system comprising:
a robot having a robot base, a robot arm coupled to the robot base, and an end-effector coupled to the robot arm, the end-effector including a guide tube for receiving at least one instrument;
a plurality of omni-directional wheels attached to the robot base allowing three-axis movement of the robot in a general area of a plane;
a plurality of sensors for detecting a desired movement of the robot base; and
a control system responsive to the plurality of sensors for controlling the three-axis movement of the robot base by actuating two or more of the plurality of omni-directional wheels.

14. The surgical robot system of claim 13, wherein each of the plurality of omni-directional wheels includes a central hub with a plurality of rollers mounted to the central hub.

15. The surgical robot system of claim 13, wherein the plurality of sensors for detecting a desired movement are selected from the group consisting of a strain gauge, force-sensing resistor, a piezoelectric sensor, a piezo capacitive pressure sensor, a piezo resistor and a microelectromechanical systems (MEMS) micro-scale strain gauge.

16. The surgical robot system of claim 13, further comprising a plurality of motors, one motor for each of the plurality of omni-directional wheels, each motor controlled by the control system for independently powering one of the plurality of omni-directional wheels.

17. The surgical robot system of claim 13, wherein the plurality of sensors are operable to sense a desired front left wheel force in a forward/backward direction, a desired rear left wheel force in the forward/backward direction, a desired rear left wheel force in a side direction, a desired front right wheel force in a forward/backward direction, a rear right wheel force in a side direction and a rear right wheel force in a backward/forward direction.

18. The surgical robot system of claim 13, wherein the plurality of sensors comprises a sensor array mounted in a planar configuration selected from the group consisting of a generally circular array, a generally elliptical array, a generally rectangular array and a generally square array.

19. A surgical robot system comprising:
a robot having a robot base and a robot arm coupled to the robot base;
a plurality of omni-directional wheels affixed to the robot base allowing multiple-axis movement of the robot;
a plurality of sensors for detecting a desired movement of the robot base; and
a control system responsive to the plurality of sensors for controlling the multiple-axis movement of the robot by actuating two or more of the plurality of omni-directional wheels;
wherein each of the plurality of omni-directional wheels includes a central hub with a plurality of rollers mounted to the central hub.

20. The surgical robot system of claim 19, wherein the plurality of rollers are mounted at an angle to a central axis of the central hub.

* * * * *